US012797114B2

(12) United States Patent
Biedermann et al.

(10) Patent No.: US 12,797,114 B2
(45) Date of Patent: Nov. 17, 2026

(54) POLYAXIAL BONE ANCHORING DEVICE

(71) Applicant: BIEDERMANN TECHNOLOGIES GMBH & CO. KG, Donaueschingen (DE)

(72) Inventors: Timo Biedermann, Trossingen (DE); Lutz Biedermann, VS-Villingen (DE); Berthold Dannecker, St. Georgen (DE); Bernd Fischer, Bräunlingen (DE)

(73) Assignee: BIEDERMANN TECHNOLOGIES GMBH & CO. KG, Donaueschingen (DE)

( * ) Notice: Subject to any disclaimer, the term of this patent is extended or adjusted under 35 U.S.C. 154(b) by 0 days.

(21) Appl. No.: 19/423,618

(22) Filed: Dec. 17, 2025

(65) Prior Publication Data

US 2026/0114906 A1 Apr. 30, 2026

Related U.S. Application Data

(63) Continuation of application No. 18/056,838, filed on Nov. 18, 2022, now Pat. No. 12,514,619, which is a (Continued)

(30) Foreign Application Priority Data

Apr. 15, 2021 (EP) .................................... 21168627

(51) Int. Cl.
*A61B 17/70* (2006.01)
*A61B 17/64* (2006.01)

(52) U.S. Cl.
CPC ...... *A61B 17/7032* (2013.01); *A61B 17/6475* (2013.01); *A61B 17/7008* (2013.01); *A61B 17/7082* (2013.01); *A61B 17/7091* (2013.01)

(58) Field of Classification Search
CPC ............ A61B 17/7032; A61B 17/7035; A61B 17/7037
See application file for complete search history.

(56) References Cited

U.S. PATENT DOCUMENTS 5,549,608 A * 8/1996 Errico ................ A61B 17/7037 606/264
5,733,285 A 3/1998 Errico et al.
(Continued)

FOREIGN PATENT DOCUMENTS

DE 102015214384 A1 * 2/2017 ......... A61B 17/7098
EP 2 204 129 A1 7/2010
(Continued)

OTHER PUBLICATIONS

Extended European Search Report for Application No. 21168627.4, mailed Oct. 8, 2021, 9 pages.

*Primary Examiner* — Eduardo C Robert
*Assistant Examiner* — Michelle C Green
(74) *Attorney, Agent, or Firm* — Womble Bond Dickinson (US) LLP

(57) ABSTRACT

A polyaxial bone anchoring device includes a receiving part with a rod receiving portion defining a recess for receiving a rod, and a head receiving portion with a wall that defines an accommodation space for accommodating a head of an anchoring element, and a locking member positionable at least partially around the head receiving portion and movable from a first position where the head can pivot in the accommodation space to a second position where an angular position of the head is locked. The wall of the head receiving portion further defines at least one cavity in communication with the accommodation space that reduces a radial thickness of at least part of the wall located between the accommodation space and the locking member, and at least part of
(Continued)

the cavity is separated radially from the accommodation space by a portion of the wall.

20 Claims, 17 Drawing Sheets

Related U.S. Application Data continuation of application No. 17/721,116, filed on Apr. 14, 2022, now Pat. No. 11,564,715.

(60) Provisional application No. 63/175,281, filed on Apr. 15, 2021.

(56) References Cited

U.S. PATENT DOCUMENTS

| | | | | |
|---|---|---|---|---|
| 6,273,888 | B1 | 8/2001 | Justis | |
| 8,506,609 | B2 | 8/2013 | Biedermann et al. | |
| 9,895,171 | B2 | 2/2018 | Webb | |
| 2005/0080415 | A1 * | 4/2005 | Keyer ................ | A61B 17/7037 606/279 |
| 2006/0089643 | A1 | 4/2006 | Mujwid | |
| 2006/0161152 | A1 * | 7/2006 | Ensign ............... | A61B 17/7032 606/279 |
| 2006/0200128 | A1 * | 9/2006 | Mueller ............. | A61B 17/7032 606/301 |
| 2008/0015576 | A1 * | 1/2008 | Whipple ............ | A61B 17/7037 606/60 |
| 2008/0108992 | A1 | 5/2008 | Barry et al. | |
| 2009/0036934 | A1 * | 2/2009 | Biedermann ...... | A61B 17/7037 606/301 |
| 2009/0069852 | A1 * | 3/2009 | Farris ................. | A61B 17/7038 606/301 |
| 2009/0149887 | A1 * | 6/2009 | Schlaepfer ......... | A61B 17/7091 606/301 |
| 2012/0165874 | A1 | 6/2012 | Biedermann et al. | |
| 2012/0179209 | A1 | 7/2012 | Biedermann et al. | |
| 2012/0179211 | A1 | 7/2012 | Biedermann et al. | |
| 2012/0283789 | A1 * | 11/2012 | Biedermann ...... | A61B 17/7034 606/308 |
| 2013/0085536 | A1 | 4/2013 | Bledermann et al. | |
| 2014/0012337 | A1 | 1/2014 | Biedermann et al. | |
| 2014/0031880 | A1 | 1/2014 | Biedermann et al. | |
| 2016/0030090 | A1 * | 2/2016 | Webb ................. | A61B 17/7037 606/266 |
| 2016/0331412 | A1 | 11/2016 | Biedermann et al. | |

FOREIGN PATENT DOCUMENTS

| | | |
|---|---|---|
| EP | 3 287 089 A1 | 2/2018 |
| EP | 3 501 436 A1 | 6/2019 |

* cited by examiner

POLYAXIAL BONE ANCHORING DEVICE

CROSS-REFERENCE TO RELATED APPLICATION(S)

This application is a continuation of U.S. patent application Ser. No. 18/056,838, filed Nov. 18, 2022, which is a continuation of U.S. patent application Ser. No. 17/721,116, filed Apr. 14, 2022, now U.S. Pat. No. 11,564,715, which claims priority to and the benefit of U.S. Provisional Patent Application No. 63/175,281, filed Apr. 15, 2021, the contents of which are hereby incorporated by reference in their entirety, and claims priority from European Patent Application EP 21 168 627.4, filed Apr. 15, 2021, the contents of which are hereby incorporated by reference in their entirety.

BACKGROUND

Field

The application relates to a polyaxial bone anchoring device with an outer locking member for locking a head of an anchoring element in a receiving part.

Description of Related Art

A polyaxial bone anchoring device is used in orthopedic surgery, in particular in spinal surgery, for coupling a rod to a bone anchor. Typically, a head of the bone anchor is pivotably received in a receiver which also connects to the rod. The receiver can assume various angular positions with respect to the bone anchor to provide a suitable orientation with respect to the rod to be connected, and the receiver and head can be locked in this orientation. Various design concepts have been developed for such polyaxial bone anchoring devices. For example, one concept is to lock the head within the receiver by means of a pressure member placed in the receiver and pressing the head firmly into a seat in the receiver. Another concept is to accommodate the head in a flexible portion of the receiver and to compress the flexible portion by means of a locking ring embracing the flexible portion so as to lock the head therein.

The concept using an outer locking ring is described, for example, in U.S. Pat. No. 5,733,285, which describes a polyaxial colletted locking mechanism for use with an orthopedic apparatus that includes a screw or other orthopedic implant element having a curvate head and a coupling element. The coupling element has a tapered and colletted portion having an interior chamber in which the curvate head is initially polyaxially disposed. A locking collar is disposed around the tapered and colletted portion such that translation thereof in the direction of the expanding taper causes the interior volume to contract onto the curvate head and lock it therein.

U.S. Pat. No. 8,506,609 B2 describes a polyaxial bone anchoring device with a receiving part for coupling a rod to a bone anchor, wherein the receiving part has a head receiving portion and a rod receiving portion. The head receiving portion is flexible for inserting and clamping the head. A locking ring extends around the head receiving portion. In a pre-locking position the locking ring exerts a first force onto the head receiving portion and the head is prevented from removal. In a locking position the locking ring exerts a second force greater than the first force onto the head receiving portion to lock the head.

Another polyaxial bone anchoring device is known from U.S. Pat. No. 9,895,171 B2. It includes a threaded screw with a head portion and a tulip assembly that selectively "snaps" and locks onto the head portion of the threaded screw in a desired orientation.

The threaded screw may be placed in bone before the tulip assembly is engaged.

SUMMARY

It is an object underlying the invention to provide an improved polyaxial bone anchoring device that is simple and safe to use and that provides a variety of features or applications.

According to an aspect of the invention, the polyaxial bone anchoring device includes an anchoring element with a shank for anchoring in bone and a head, a receiving part having a head receiving portion with a wall defining an accommodation space for accommodating the head of the anchoring element and a central axis extending through the accommodation space. The polyaxial bone anchoring device further includes a locking member mountable to the receiving part such that it at least partially embraces the wall of the head receiving portion and is movable between at least a first position and a second position, wherein the head receiving portion is configured to assume at least a first configuration in which the head can pivot in the accommodation space when the locking member is in the first position and a second configuration in which the head is locked in the accommodation space when the locking member is in the second position. The head receiving portion has at least one cavity in the wall that is configured such that a thickness of the wall in a radial direction with respect to the central axis between the accommodation space and the locking member is reduced by the cavity.

Since the head receiving portion has a partially reduced wall thickness, the spreading of the head receiving portion may be more easily facilitated. Thus, the receiving part may be mounted more easily onto the head of the bone anchor. On the other hand, another thicker wall portion forming a seat against which the head is pressed by action of the locking member has a sufficient strength and stability against loosening of the clamping.

The polyaxial bone anchoring device includes only few parts, which renders it more convenient to handle.

Moreover, the cavity in the head receiving portion enables other applications and/or uses. For example, in one embodiment, pharmaceutical substances may be deposited in the cavity. Once the polyaxial bone anchoring device has been implanted into a patient's body, the pharmaceutical substances may be released over time. In another embodiment, the cavity may be used for accommodating a spring portion of a pressure member that is resiliently connected to the receiving part.

According to another aspect of the invention, a polyaxial bone anchoring device includes an anchoring element with a shank for anchoring in bone and a head, a receiving part having a head receiving portion defining an accommodation space for accommodating the head of the anchoring element, and a pressure member which is configured to exert pressure onto the head in the accommodation space, wherein the pressure member is configured to assume at least a first position in which the head can pivot in the accommodation space and a second position in which the head is locked in the accommodation space, and wherein the pressure member is monolithic with the receiving part. In a particular embodiment, the pressure member is movable from the first position to the second position by separating the pressure member from the receiving part, preferably at a predefined breaking region. In another particular embodiment, the pressure member is resiliently connected with the receiving part.

In a still further embodiment a method of manufacturing a polyaxial bone anchoring device is provided, wherein the method includes manufacturing the receiving part with the cavity and/or with the pressure member by means of an additive manufacturing method, such as three dimensional printing, for example, laser sintering or laser or electron beam melting. With such a method, complex shapes can be easily manufactured on the basis of CAD data of the object to be manufactured. Hence, the cavity of the head receiving portion and/or the pressure member can be designed to have any shape regardless of conventional manufacturing restrictions.

BRIEF DESCRIPTION OF THE DRAWINGS

Further features and advantages of the invention will become apparent from the detailed description of embodiments by means of the accompanying drawings. In the drawings:

FIGS. 11*a* to 11*e* show cross-sectional views of steps of assembling the polyaxial bone anchoring device of FIGS. 1 to 3, wherein FIG. 11*c* shows an enlarged view of a detail of FIG. 11*b*.

FIGS. 12*a* to 12*f* show cross-sectional views of steps of locking the head of the bone anchor in the receiving part of the assembled polyaxial bone anchoring device of FIGS. 1 to 3, wherein FIG. 12*b* shows an enlarged view of a detail of FIG. 12*c* and FIG. 12*d* shows a further enlarged view of a detail of FIGS. 12*b* and 12*c*.

DETAILED DESCRIPTION

Figure 1:
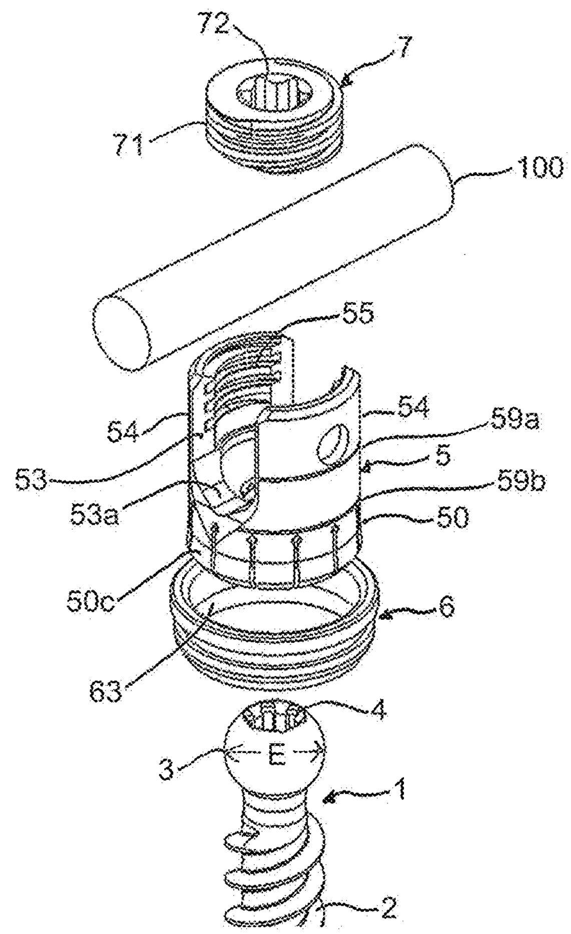
FIG. 1 shows a perspective exploded view of an embodiment of a polyaxial bone anchoring device.
Figure 2:
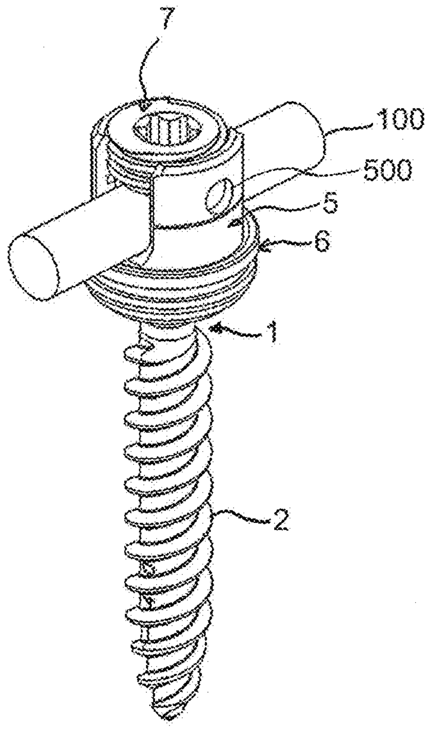
FIG. 2 shows the polyaxial bone anchoring device of FIG. 1 in an assembled state.
Figure 3:
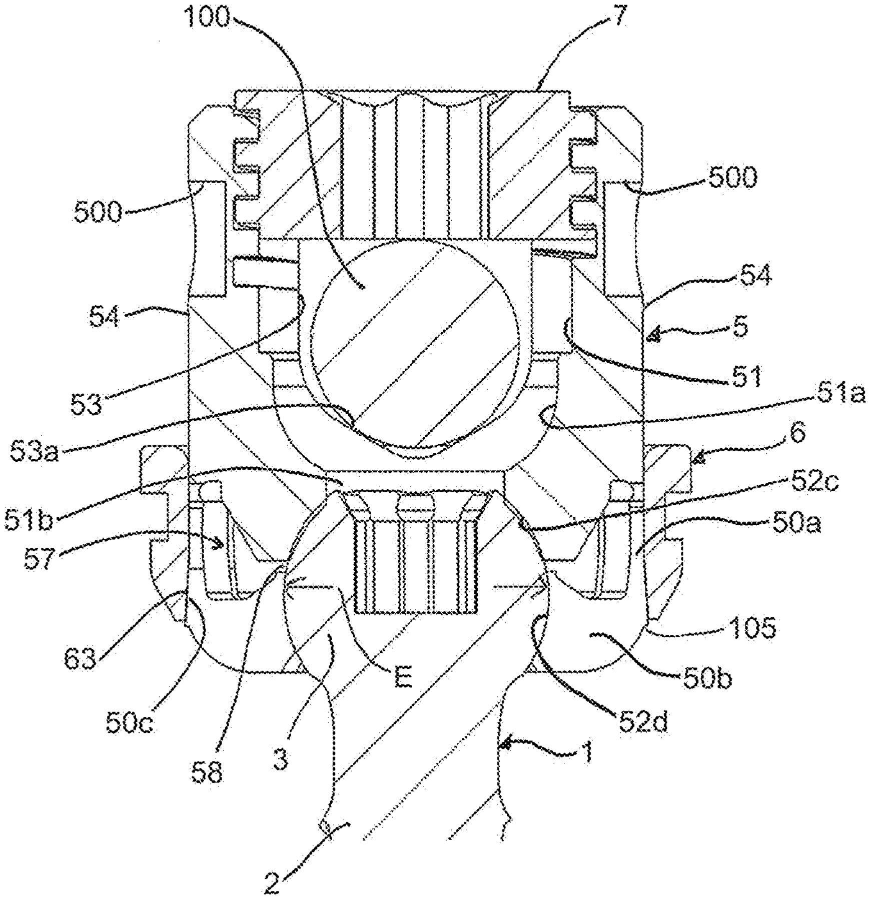
FIG. 3 shows a cross-sectional view of the polyaxial bone anchoring device of FIGS. 1 and 2 in an assembled state, the cross-section being taken in a plane extending through centers of legs of the receiving part and perpendicular to an inserted rod.
Figure 4:
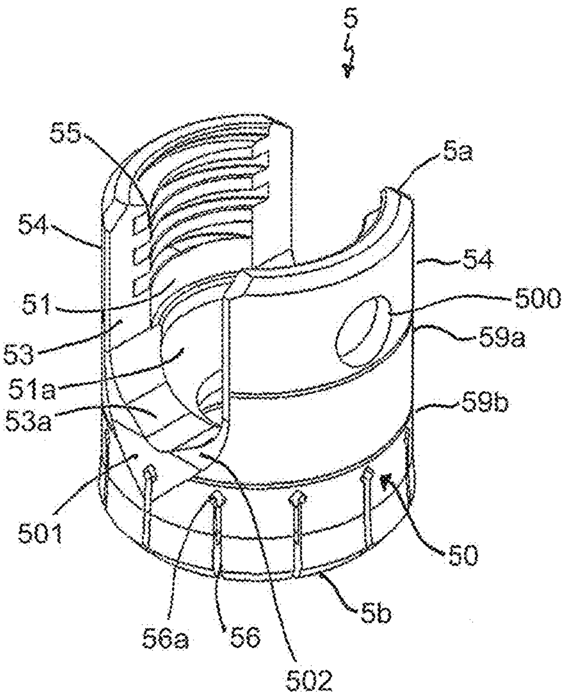
FIG. 4 shows a perspective view from a top of a receiving part of the polyaxial bone anchoring device of FIGS. 1 to 3.
Figure 5:
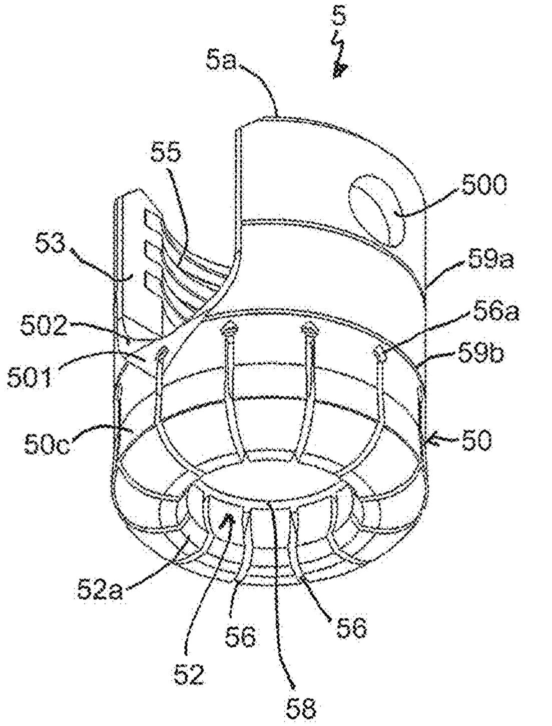
FIG. 5 shows a perspective view from a bottom of the receiving part of FIG. 4.
Figure 6:
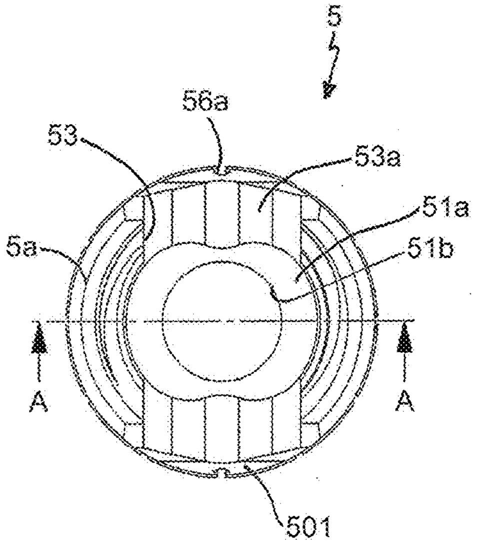
FIG. 6 shows a top view of the receiving part of FIGS. 4 and 5.
Figure 7:
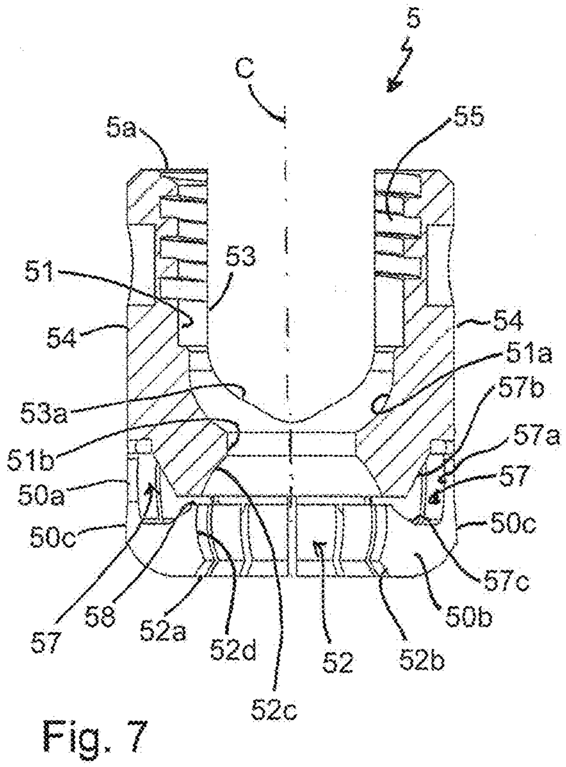
FIG. 7 shows a cross-sectional view of the receiving part of FIGS. 4 to 6, the cross-section being taken along line A-A in FIG. 6.

Referring to FIGS. 1 to 3, an embodiment of the polyaxial bone anchoring device includes an anchoring element 1 having a shank 2 and a head 3. The anchoring element 1 may be in the form of a bone screw with the shank 2 being at least partially threaded. The head 3 has a spherical outer surface portion. More specifically, the head 3 may be formed as a spherical segment, preferably including a region of a greatest outer diameter E of the sphere. In a free end surface of the head 3 opposite to the shank 2, a recess 4 for engagement with a drive tool may be provided. The polyaxial bone anchoring device further includes a receiving part 5 which is configured to accommodate the head 3 of the anchoring element and for receiving a rod 100. The rod 100 serves to connect the polyaxial bone anchoring device to at least one further bone anchor which may be part of an identical or similar polyaxial bone anchoring device. A locking member in the form of a locking ring 6 serves for locking the head 3 in the receiving part 5 with the shank 2 at a particular angular position. To fix the rod 100 in the receiving part 5, a fixation member 7 may also be part of the polyaxial bone anchoring device. The fixation member 7 has an engagement structure 71 and a tool engagement recess 72. The fixation member may be, for example, a set screw that can be screwed into the receiving part 5.

Referring further to FIGS. 4 to 7, the receiving part 5 has a first or upper end 5*a* and a second or lower end 5*b*, and a substantially cylindrical outer shape that extends around a central axis C. A coaxial passage 51 extends from the first end 5*a* to a distance therefrom. The passage 51 narrows in a narrowing portion 51*a* towards a reduced diameter intermediate portion 51*b*. The narrowing portion 51*a* may be spherical but can also have another shape such as, for example, a conical shape. Adjacent to the intermediate portion 51*b*, an accommodation space 52 is formed that is shaped and sized to accommodate the head 3 therein. The accommodation space 52 has an opening 52*a* at the second end 52. A substantially U-shaped recess 53 extends from the first end 5*a* to a distance therefrom, by means of which two upstanding legs 54 are formed. The legs 54 define a channel for receiving the rod 100. A bottom 53*a* of the channel may have a substantially V-shaped upper contour which provides a rod support surface. By means of this, rods with different diameters can be inserted into the channel and can be more securely supported on the rod support surface. Any rod with a diameter between a greatest diameter and a smallest diameter that are respectively defined by the size of the recess 53 and by the shape of the bottom 53*a* can more safely and securely rest on the bottom 53*a*. An internal thread 55 is formed on the legs 54 which is configured to cooperate with the external thread 71 of the fixation member 7. The internal thread 55 may have any suitable threadform, preferably however, a threadform that prevents splaying of the legs 54 when the fixation member is tightened. For example, the threadform may be a flat thread or a square thread. By means of the U-shaped recess 53, the upper portion of the receiving part defines a rod receiving portion.

A lower portion of the receiving part 5, approximately from the intermediate portion 51*b* of the passage 51 to the second end 5*b*, which includes the accommodation space 52, defines a head receiving portion 50 of the receiving part 5. The accommodation space 52 has a substantially spherical inner contour that matches an outer contour of the head 3. The axial extension of the accommodation space 52 is such that it is configured to cover the region of the head 3 with the greatest outer diameter E. More specifically, the size of the accommodation space 52 may be such that the head 3 can be held therein by friction. A small outwardly tapering portion 52*b* that widens towards the second end 5*b* may be provided for facilitation of the insertion of the head and/or for providing a slightly greater range of pivot angles for the shank 2. As can be seen in particular in FIGS. 3 and 7, the accommodation space 52 is divided into an upper portion 52*c* configured to cover the head 3 from the top, and a lower portion including a seat 52*d* for the head 3 in which the head 3 can pivot.

A wall of the receiving part 5 around the accommodation space 52 for the head 3 is expandable and compressible in a radial direction with respect to the central axis C. This is achieved by a plurality of axially extending slits 56 that are open to the second end 5*b* and that may extend up to a distance from the second end, preferably up to the intermediate portion 51*b* of the passage 51. The size and number of the slits 56 may be selected to obtain a desired flexibility. Moreover, an end portion 56*a* of the slits 56 may be enlarged, for example with a diamond-shaped contour, a circular contour, or a triangular contour, or any other suitable shape.

A cavity 57 is formed in the wall circumferentially around the accommodation space 52. The cavity 57 may extend in the axial direction from a position below a region accommodating the greatest diameter E of the head up to the end portions 56*a* of the slits 56, as can be seen in particular in FIG. 3. Thus, the cavity 57 encircles an inserted head circumferentially and extends along a substantial region of the head 3 in the axial direction. Moreover, the cavity 57 is in communication with the accommodation space 52 through an opening 58 which has a smaller height in the axial direction than a radially outer portion of the cavity 57. More specifically, the opening 58 has the shape of an annular slit as can be seen in particular in FIGS. 5 and 7. An outwardly directed wall portion 57*a* defining the cavity 57 may make the cavity 57 slightly convex and may be formed at a radial position away from the central axis C, so that a radially outermost wall portion 50*a* of the head receiving portion 50 is thinner than a lowermost wall portion 50*b* below the cavity 57 at or adjacent to the second end 5*b*. Also, the end portions 56*a* of the slits 56 are in communication with the cavity 57. An upper wall portion 57*b* of the wall defining the cavity may be inclined and tapered to narrow towards the second end 5*b* up to the opening 58. A lower wall portion 57*c* of the wall defining the cavity 57 may have a portion that is substantially flat in a direction substantially perpendicular to the central axis and may have another portion that rises in a curved or inclined manner that narrows towards the opening 58. It shall be noted that the detailed shape of the cavity is not limited to the embodiment shown but may vary. More generally, the axial height of the cavity 57 is greatest at a particular radial distance from the central axis C and decreases towards the central axis C.

By the opening 58 of the cavity 57, the accommodation space 52 is divided into the upper portion 52*c* and the seat 52*d* which can be pressed against the head 3 by the locking ring 6.

The wall portion 50*a* is thin compared to the wall portion 50*b* in the radial direction. Moreover, the wall portion 50*b* is divided in the circumferential direction by the slits 56 into a plurality of sections which behave as flexible wall sections. Due to the cavity 57, the flexible wall sections of the wall portion 50*b* can be easily spread, although they are relatively thick at the second end 5*b* of the receiving part. When the head receiving portion 50 is compressed by the locking ring 6, as described below, the lowermost wall portion 50*b* is configured to exert pressure onto the head 3 from an axial position at or close to the region with the greatest diameter E of the head and from below this region, as depicted in FIG. 3. As the wall sections of the wall portion 50*b* are thicker, a sufficiently strong clamping force can be achieved. Also, the strength against loosening may be enhanced by this design.

In other words the wall sections provide a stable seat 52*d* for the head 3 in which the head can be safely clamped.

The outer surface of the wall of the head receiving portion 50 widens in a tapered portion 50*c* close to the second end 5*b* towards the second end 5*b*. Thereby, the compression force increases when the locking ring 6 is moved along the head receiving portion 50 in a direction towards the second end 5*b*. Except for the tapered portion 50*c*, the outer diameter of the receiving part 5 may be substantially the same along the axial length of the receiving part 5. Between the tapered portion 50*c* and the second end 5*b*, the outer surface may be convexly rounded, and an edge 105 may be formed between the rounded surface and the tapered portion 50*c*.

At an axial position above the bottom 53*a* of the U-shaped recess 53 and at a distance from the first end 5*a*, a first holding structure for temporarily holding the locking ring 6 at an insertion position in which the head is insertable into the accommodation space 52 is provided. At the outside of each leg 54, the first holding structure may be in the form of a circumferentially extending first rib 59*a*. A thickness of the first rib 59*a* in the radial direction is such that when the locking ring 6 passes the first rib 59*a*, the locking ring experiences a friction force such that the locking ring 6 is held by friction in the respective axial position. As also shown in FIGS. 11*b* and 11*c*, the position of the first holding structure may be such that the locking ring 6 can be held completely above the head receiving portion 50.

A second holding structure is provided at a distance from the first holding structure towards the second end 5*b*. The second holding structure may also be in the form of a circumferential rib 59*b* at the outer surface of the receiving part 5. The axial position of the second holding structure may be slightly below the bottom 53*a* of the substantially U-shaped recess 53 and above the end portion 56*a* of the slits. Also the second circumferential rib 59*b* has a thickness such that the locking ring 6 experiences a friction force when it passes along the outer surface of the receiving part. Thereby, the locking ring 6 can be held temporarily at a pre-locking position in which the head receiving portion 50 is compressed but the head 3 is still pivotable without being finally locked. As additionally shown in FIG. 12*a*, in the pre-locking position, the locking ring 6 still has not fully engaged the tapered outer surface portion 50*c* of the head receiving portion 50. In the pre-locking position, the head 3 is prevented from removal through the lower opening 52*a* of the accommodation space 52.

At the center of each leg 54 in a circumferential direction, a through hole 500 or another engagement recess may be provided for engagement with an instrument. Lastly, inclined cutaway portions 501 may be formed at either end of the channel for the rod close to the bottom 53*a* of the substantially U-shaped recess. The cutaway portions 501 may extend until below the end portions 56*a* of the slits and may have a substantially triangular contour with the tip oriented towards the second end 5*b*. Additional chamfered portions 502 may extend from the cutaway portions 501 to some extent towards the edges of each of the legs 54 on either side of the channel. The cutaway portions 501 and chamfered portions 502 may facilitate the mounting of the locking ring from the first end 5*a* of the receiving part 5 and/or generally reduce the size of the receiving part.

Figure 8:
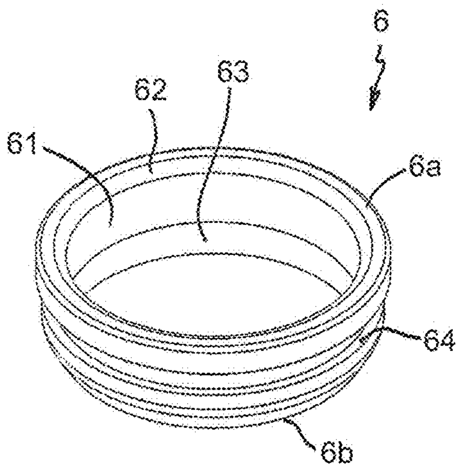
FIG. 8 shows a perspective view of a locking member in the form of a locking ring of the polyaxial bone anchoring device of FIGS. 1 to 3.
Figure 9:
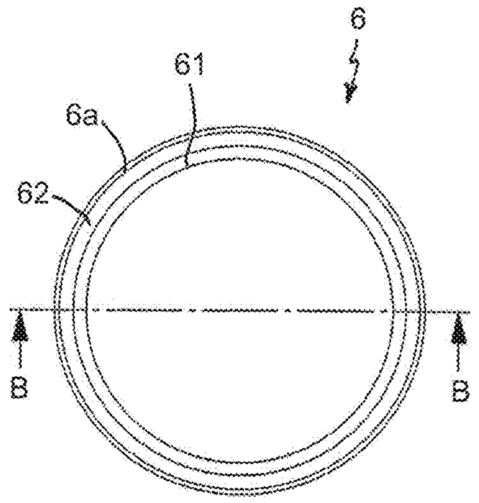
FIG. 9 shows a top view of the locking ring of FIG. 8.
Figure 10:
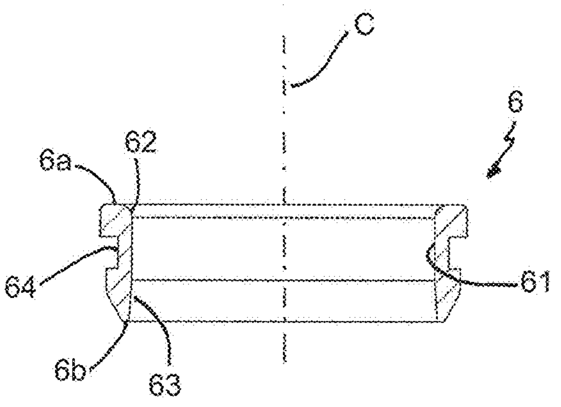
FIG. 10 shows a cross-sectional view of the locking ring of FIGS. 8 and 9, the cross-section being taken along line B-B in FIG. 9.

Referring additionally to FIGS. 8 to 10, the locking ring 6 will be described in greater detail. The locking ring 6 is formed as a closed ring with a first or upper end 6*a* and a second or lower end 6*b*. The inner surface 61 is substantially cylindrical with an inner diameter sized such that the locking ring 6 fits around the receiving part 5 and is configured to slide along the outer surface of the receiving part 5. Adjacent to the first end 6*a*, a small beveled portion 62 may be formed that may serve for sliding the locking ring from the second end 5*b* of the receiving part along the rounded outer surface of the lower wall 50*b* and over the tapered portion 50*c* for mounting. Adjacent to the second end 6*b*, the locking ring 6 may include a tapered inner surface portion 63 that tapers and narrows towards the first end 6*a* and is configured to cooperate with the tapered outer surface portion 50*c* of the receiving part 5. The angles of the tapered portions of the locking ring 6 and the receiving part 5 preferably correspond to each other. Preferably the angle is selected such that a self-locking occurs when the surfaces engage each other. Thus, once the locking ring 6 is mounted and the tapered surfaces engage each other, the locking ring is restricted from being inadvertently moved upward and loosening the locking. However, it may be possible to disengage the cooperating surfaces, for example, by using an instrument.

The outer surface of the locking ring 6 has a groove 64 that may serve for engagement with an instrument. Adjacent to the first end 6*a*, the outer surface may be cylindrical and adjacent to the second end 6*b* the outer surface may be tapered and narrow towards the second end 6*b*. However, the shape is not limited to such a design.

The axial length of the locking ring 6 may be at least the axial length of the cavity 57, and preferably greater than the axial length of the cavity 57. Thus, the locking ring is configured to exert a radial compression force onto a major part of the head receiving portion 50.

The locking ring 6 can also be mounted to the receiving part 5 from the first end 5*a* thereof. In this case, the tapered portion 63 can slide along rounded edges of the legs 54 at the first end 5*a* of the receiving part 5.

Parts and portions of the polyaxial bone anchoring device may be made of any material, preferably, however, of a bio-compatible material, such as titanium or stainless steel, or of any other bio-compatible metal or metal alloy, or of a plastic material. For bio-compatible alloys, a NiTi-alloy, for example Nitinol, may be used. Other materials that can be used are Magnesium or Magnesium alloys, and bio-compatible plastic materials that can be used may be for example, Polyether ether ketone (PEEK) or Poly-L-lactide acid (PLLA). The parts can be made of the same or of different materials from one another.

A preferred method of manufacturing the receiving part and optionally also the locking ring and/or the bone anchoring element is an additive manufacturing method, more preferably an additive layer manufacturing method, such as three-dimensional printing. More particularly, preferred methods are laser sintering or laser melting or electron beam melting. In such methods, subsequent layers of a powder material, such as a metal or plastic powder, are solidified with an energy beam, particularly a laser or an electron beam, at positions corresponding to the cross-section of each part at each respective layer. By such a method, complex shapes including undercuts, etc., can be more easily manufactured.

Figure 11A:
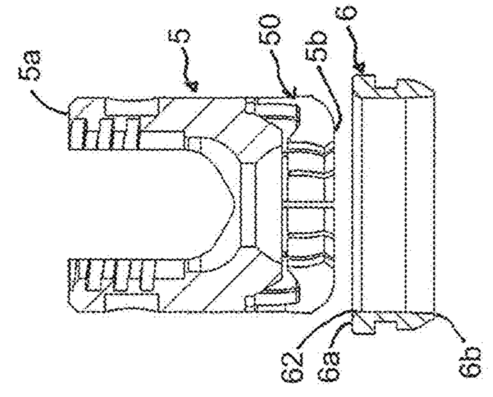
Figure 11B:
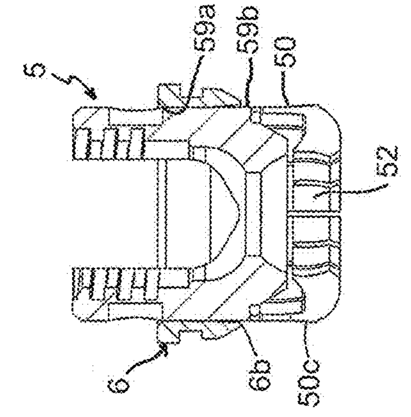
Figure 11C:
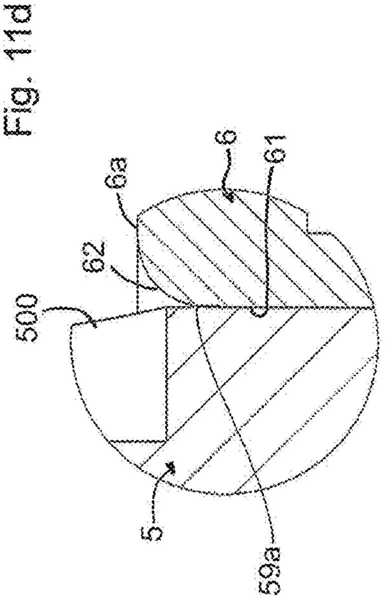
Figure 11D:
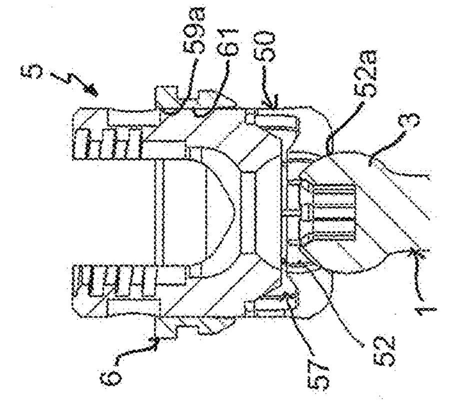
Figure 11E:
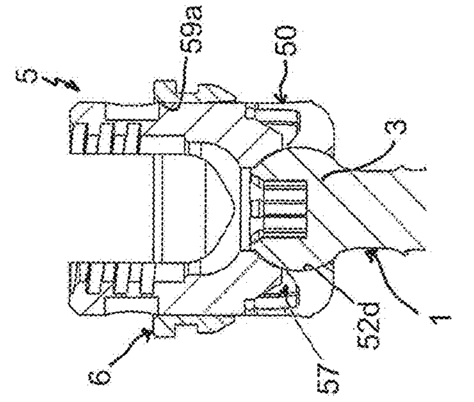

Referring to FIGS. 11*a* to 11*e*, steps of mounting the locking ring 6 to the receiving part 5 and assembling the polyaxial bone anchoring device will be explained. According to a first method of assembling, the locking ring 6 is mounted to the receiving part 5 from the second end 5*b* of the receiving part 5. As shown in FIG. 11*a*, the locking ring 6 is oriented with its first end 6*a* towards the second end 5*b* of the receiving part and subsequently pushed onto the receiving part 5 as shown in FIG. 11*b*. During this step, the beveled portion 62 slides along the rounded lower surface of the receiving part 5 and compresses the head receiving portion 50 slightly so that the locking ring can move over the edge 105 between the rounded portion and the tapered portion 50*c*. Then, the locking ring 6 can be moved further towards the first end 6*a*. The locking ring passes the second rib 59*b* which is slightly retracted due to the compression of the head receiving portion so that it does not present an obstacle during mounting. When the locking ring 6 reaches the first rib 59*a*, the locking ring is held there by the friction that occurs between the first rib 59*a* and an upper region of the cylindrical section 61 of the locking ring that is close to the beveled portion 62, as shown in FIG. 11*c*. In this position, which is an insertion position of the locking ring for permitting the head 3 to be inserted into the accommodation space 52, the second end 6*b* of the locking ring is above the head receiving portion 50. Hence, the head receiving portion 50 is free to expand to permit the head 3 to be inserted, as shown in FIG. 11*d*. Due to the flexibility of the wall of the head receiving portion 50, the head 3 can be easily inserted and is held in the seat 52*d* by the friction force of the flexible wall sections, as shown in FIG. 11*e*.

Alternatively to the steps shown in FIGS. 11*a* and 11*b*, in some embodiments, the locking ring can also be mounted from the first end 5*a* of the receiving part.

Figure 12F:
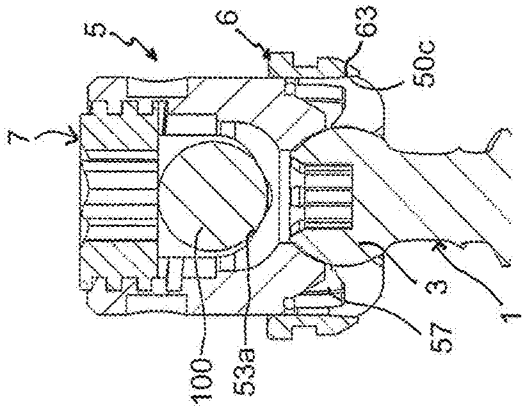
Figure 12E:
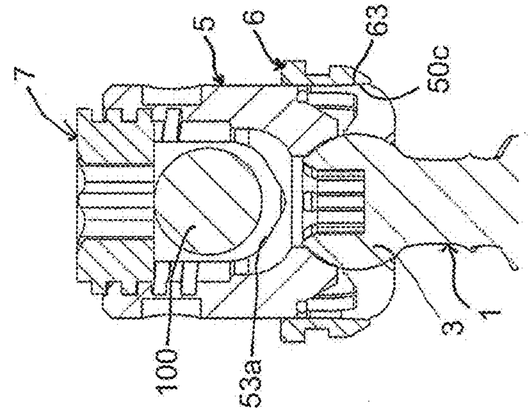
Figure 12C:
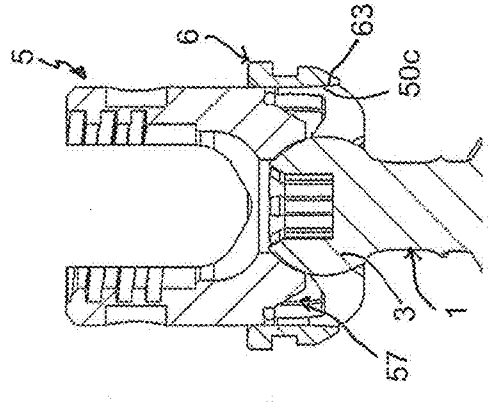
Figure 12D:
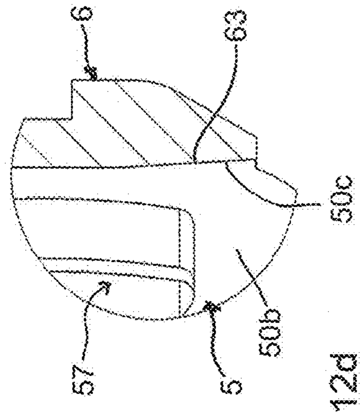
Figure 12A:
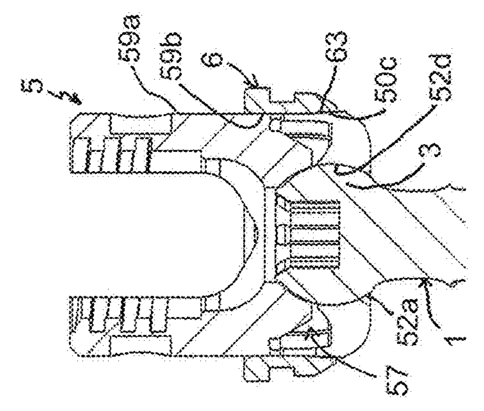

Referring to FIGS. 12*a* to 12*d*, the further steps of locking the head 3 in the receiving part 5 will be explained. In FIG. 12*a*, once the head 3 has been inserted into the accommodation space 52, the locking ring 6 is moved towards the second end 5*b* of the receiving part, whereby the friction force between the first rib 59*a* and the locking ring 6 is overcome, until the locking ring 6 passes the second rib 59*b* where the locking ring is held temporarily by friction. This position of the locking ring 6 is a pre-locking position where the head receiving portion 50 is compressed to an extent such that the head 3 cannot be removed through the opening 52*a*. Depending on the size of the head and the size and flexibility of the accommodation space, the head 3 may also be held with friction in the pre-locking position. This allows the head 3 to be held at a preliminary angular position relative to the receiving part. The preliminary angular position can be changed by overcoming the friction force, either manually or with an instrument.

Figure 12B:
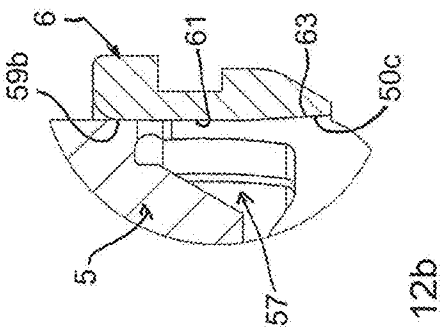
Figure 13:
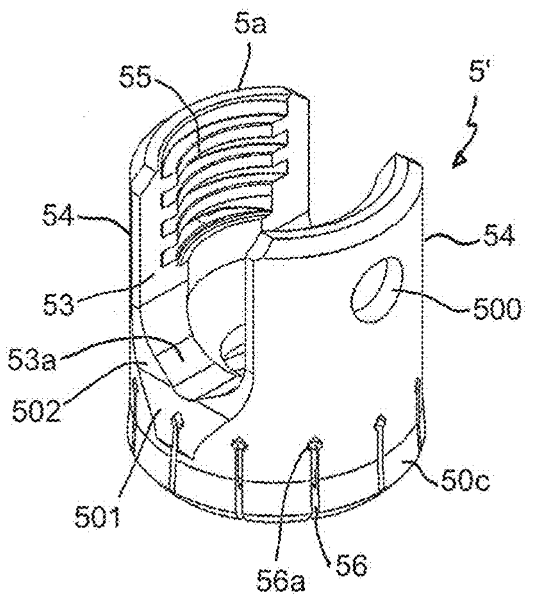
FIG. 13 shows a perspective view from a top of a receiving part of a polyaxial bone anchoring device according to a modified embodiment.
Figure 14:
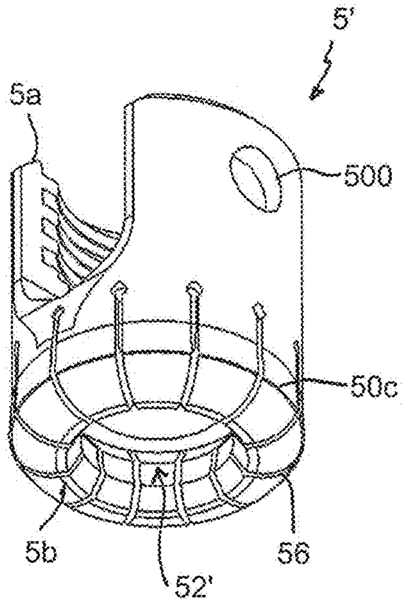
FIG. 14 shows a perspective view from a bottom of the receiving part of FIG. 13.
Figure 15:
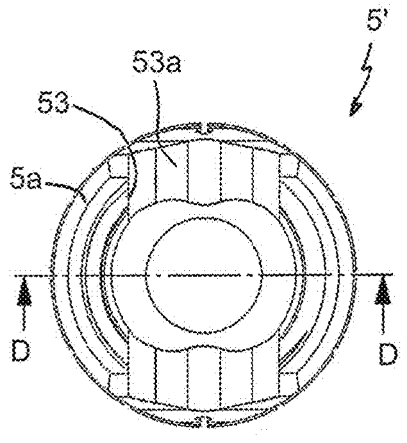
FIG. 15 shows a top view of the receiving part of FIGS. 13 and 14.
Figure 16:
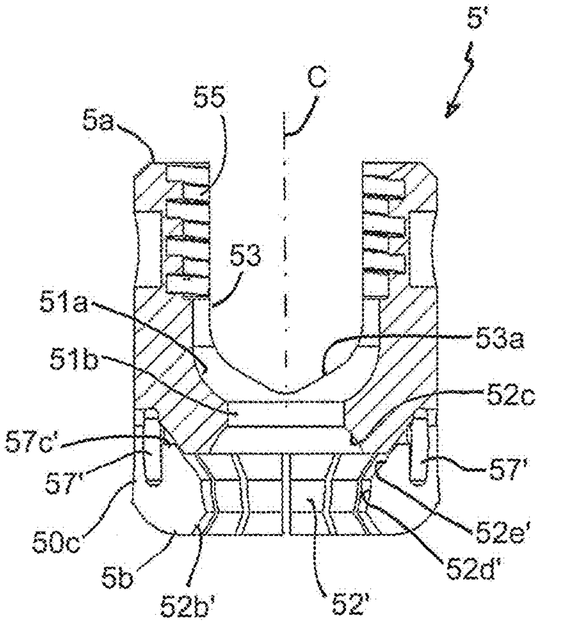
FIG. 16 shows a cross-sectional view of the receiving part of FIGS. 13 to 15, the cross-section being taken along line D-D in FIG. 15.
Figure 17:
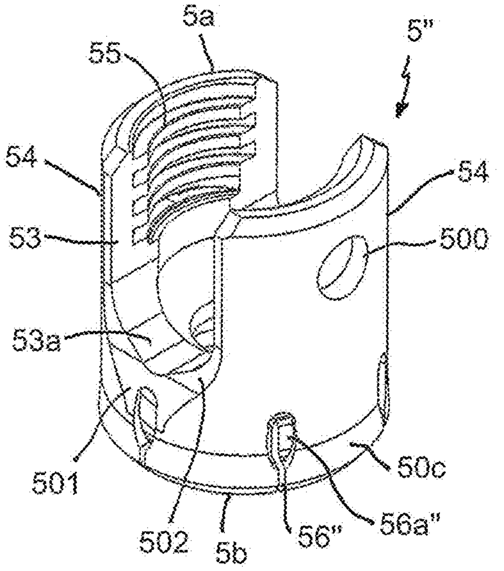
FIG. 17 shows a perspective view from a top of a receiving part of a polyaxial bone anchoring device according to a further modified embodiment.
Figure 18:
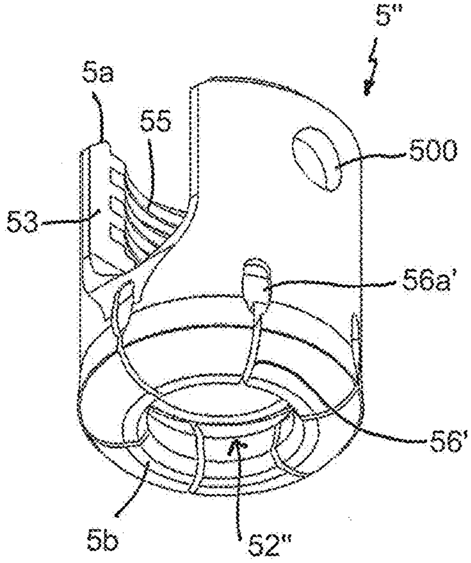
FIG. 18 shows a perspective view from a bottom of the receiving part of FIG. 17.
Figure 19:
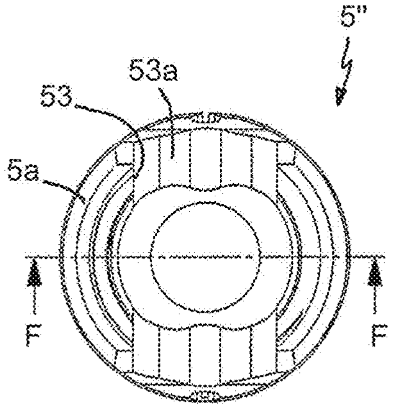
FIG. 19 shows a top view of the receiving part of FIGS. 17 and 18.
Figure 20:
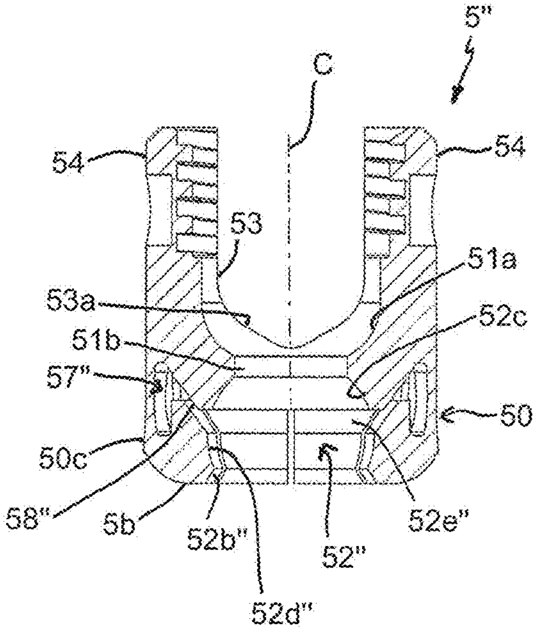
FIG. 20 shows a cross-sectional view of the receiving part of FIGS. 17 to 19, the cross-section being taken along line F-F in FIG. 19.

For locking the head 3 in the head receiving portion 50, the locking ring 6 is further moved towards the second end 5*b* until the tapered outer surfaces 63, 50*c* of the locking ring and the receiving part, respectively, substantially engage each other, as depicted in FIGS. 12*b* to 12*d*. This results in an increased compression of the head receiving portion 50 around the head 3, so that the head 3 is finally locked in the head receiving portion 50. The angle of the tapered surfaces preferably results in a self-locking, which means that the friction force between the two surfaces is high enough to prevent disengagement of the surfaces, and thereby, upward movement of the locking ring under normal conditions of use. As shown in the enlarged views of FIGS. 12*b* and 12*d*, the tapered surfaces are in full engagement when the lower end 6*b* of the locking ring is substantially flush with the lower end of the tapered surface 50*c*. Hence, the force that compresses the head receiving portion is transmitted mainly at the lower stable wall section 50*b* in a radial direction to lock the head 3 in the seat 52*d*.

After locking the head 3, the rod 100 can be inserted into the substantially U-shaped recess 53 and the fixation member 7 can be inserted between the legs 54. For final locking, as shown in FIG. 12*f*, the fixation member 7 is tightened to press the rod 100 into the bottom 53*a* of the substantially U-shaped recess 53. As the rod 100 may also press onto the first end 6*a* of the locking ring 6, depending on the size of the rod, the compression force exerted by the locking ring may increase. In this manner, the entire polyaxial bone anchoring device can be finally locked.

In clinical use, at least two polyaxial bone anchoring devices are inserted into bone parts or vertebrae and connected through the rod 100. It shall be noted that the polyaxial bone anchoring device can be used in a pre-assembled condition where the head is already inserted into the head receiving portion and with the locking ring being in the pre-locking position, as shown in FIG. 12*a*. The polyaxial bone anchoring device can be inserted in this pre-assembled condition into bone. In another way of use, the bone anchoring element 1 can be inserted first into the bone or vertebra, and the receiving part 5 with the locking ring in the insertion position as shown in FIGS. 11*b* and 11*d* is mounted to the head 3. The cavity may also be used for depositing a pharmaceutical substance therein that is released over time.

Referring to FIGS. 13 to 16, a modified receiving part of the polyaxial bone anchoring device will be explained. The receiving part 5' differs from the receiving part of the previous embodiment mainly in the design of the cavity and the accommodation space. Also, in this modified embodiment, the preliminary holding structures like the first rib and the second rib are omitted. Parts and portions of the receiving part 5' that are identical or similar to the parts and portions of the receiving part 5 of the previous embodiment are designated with the same reference numerals, and the descriptions thereof will not be repeated.

In the embodiment in FIGS. 13 to 16, the accommodation space 52' forms a seat 52*d*' that is shorter in the axial direction compared to the seat 52*d* of the previous embodiment. The widening portion 52*b*' may have an axial length that is greater than in the receiving part of the previous embodiment. Generally, the widening portion 52*b*' and the seat 52*d*' may have approximately the same axial length. Adjacent to the seat 52*d*' on a side opposite the widening portion 52*b*', there may be a conical portion 52*e*' that widens towards the first end 5*a* of the receiving part 5'. The cavity 57' is elongate in the axial direction. More specifically, the height of the cavity 57' in the axial direction is greater than the width of the cavity in the radial direction. Thus, the shape of the cavity 57' is approximately that of a hollow cylindrical ring or an oblong torus, which is located substantially at an axial position around the widening portion 52*e*' and the upper portion 52*c* of the accommodation space 52'. The opening 58' that connects the cavity 57' with the accommodation space 52' in this embodiment extends from an upper portion of the cavity 57' closer to the first end 5*a* of the receiving part into the widening portion 52*e*'. The lower wall portion 57*c*' of the cavity is located at the middle or around the middle portion of the cavity 57' in the axial direction. Thus, the cavity 57' is separated to a greater extent from the accommodation space 52', for example, compared to the previous embodiment.

The locking ring 6 can be temporarily held in the insertion position or in the pre-locking position only by friction with the outer surface of the receiving part 5'.

Referring to FIGS. 17 to 20, a further modified embodiment of the receiving part will be described. The receiving part 5" of the polyaxial bone anchoring device differs from the receiving part 5' of the previous embodiment in the design of the cavity, the accommodation space and the slits. The cavity 57" is similar to the cavity 57' of the previous embodiment. That means, the cavity 57" is substantially hollow cylindrical ring-shaped or torus-shaped and extends around the widening portion 52*e*" and the upper section 52*c* of the accommodation space. An inclined circumferential slit 58" forms the opening that connects the upper portion of the cavity 57" with the accommodation space 52". The accommodation space 52" may have an small widening section 52*b*". Different from the previous embodiments, the number and length of the slits 56" is reduced. In the embodiment shown, six equidistantly arranged slits 56" are provided compared to more slits in the previous embodiments. However, the number of slits is not restricted thereto. A smaller number of slits may result in larger wall portions in the circumferential direction. Hence, to obtain enough flexibility, the area of the end portions 56*a*" can be increased, for example, the end portions 56*a*" are elongate in the axial direction. Therefore, the head receiving portion 50 has sufficient flexibility to be easily expanded and compressed around the head 3. With the cavity 57" designed in this manner, the entire axial length of the receiving part, and mainly that of the head receiving portion 50, can be reduced, contributing to a smaller size of the receiving part 5".

Referring to FIGS. 21 to 27 a further embodiment of the polyaxial bone anchoring device will be described. The polyaxial bone anchoring device in FIGS. 21 to 27 differs from the previous embodiment in the design of the receiving part. The receiving part 5''' is similar to the receiving part 5 of the first embodiment with respect to the lower portion of the accommodation space 52 and with respect to the shape and position of the cavity 57.

Figure 21:
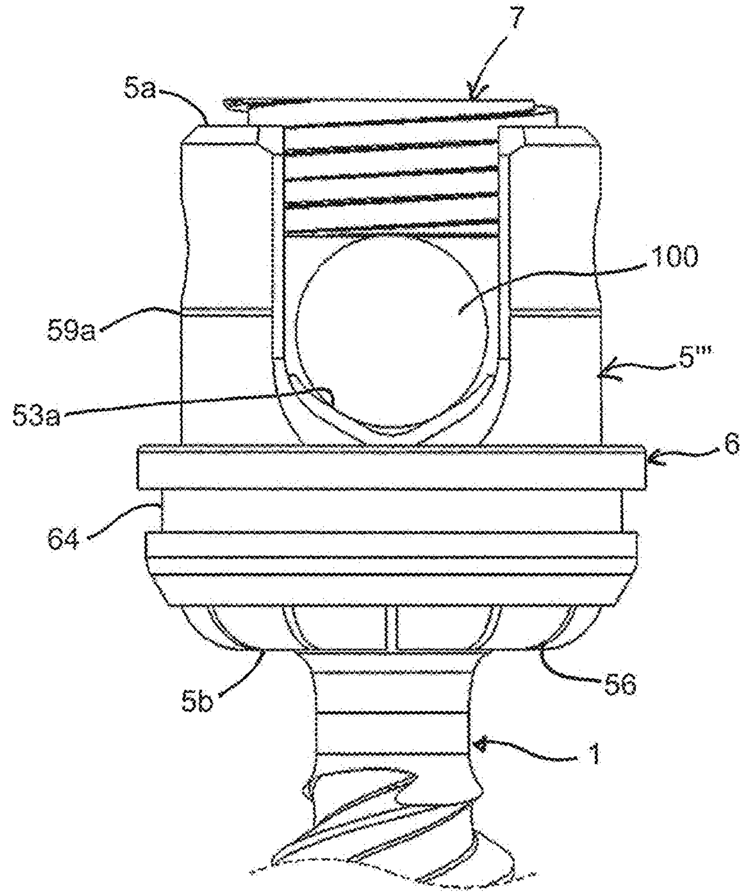
FIG. 21 shows a side view of another embodiment of a polyaxial bone anchoring device in an assembled state.

The passage 51''' accommodates a pressure member 8 that is configured to exert pressure onto the head 3 from the top of the head 3. The pressure member 8 is a substantially cylindrical part that is sized such that it fits into the passage 51''' but is not tightly guided by the wall of the passage. The pressure member has a first or upper end 8*a* and an opposite second or lower end 8*b*. At the second end 8*b*, there is a substantially spherically-shaped recess 81 with a radius corresponding to the radius of the head 3 that allows engagement with the upper surface of the head 3 and exerts pressure thereto. At the first end 8*a*, there is an elongate recess 82 with a longitudinal axis that is substantially perpendicular to the central axis C. The recess 82 has a substantially V-shaped cross-section to provide a support surface for rods of different diameters. Close to the first end 8*a*, there are circumferentially extending projections 83, in the embodiment two projections, that are axially spaced from each other and that are configured to engage corresponding circumferentially extending grooves 503 provided at the inner surface of the receiving part at an axial position such that, when the head is inserted, the inner surface of the spherical recess 81 may not yet contact the upper surface of the head 3. The projections 83 fit into the grooves 503 with axial and radial play. The recess 82 is aligned with the substantially U-shaped recess 53 of the receiving part so that the rod 100 can be inserted into the receiving part and rests on the rod support surface formed by the recess 82. Moreover, the pressure member 8 is at a position in the receiving part 5" such that the rod support surface formed by the recess 82 is slightly above the rod support surface 53*a* of the substantially U-shaped recess 53 of the receiving part 5''', as shown in FIG. 21.

Figure 23:
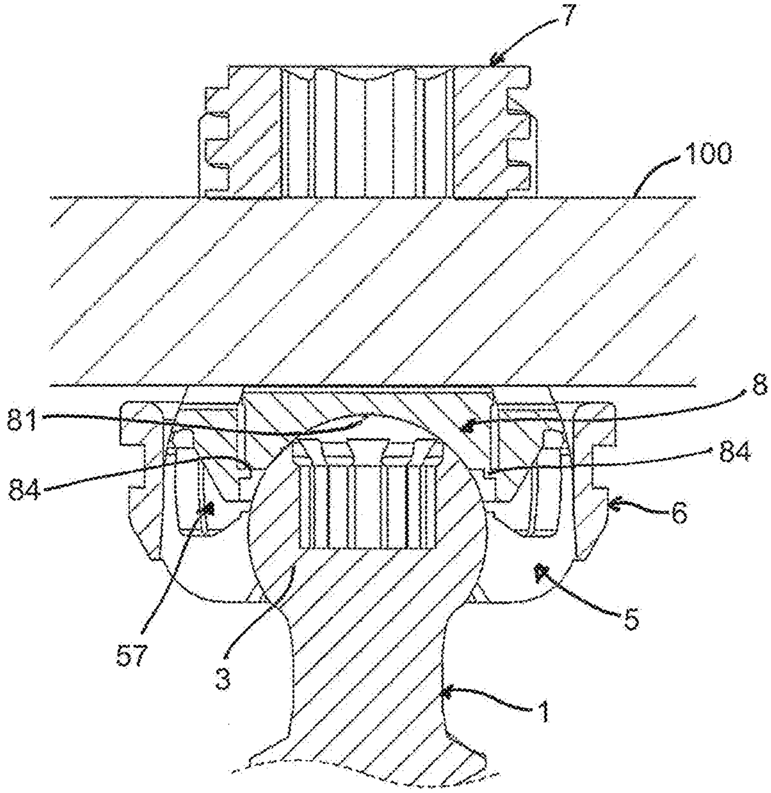
FIG. 23 shows a cross-sectional view of the polyaxial bone anchoring device of FIGS. 21 and 22, the cross-section being taken in a plane extending through a rod channel of the receiving part and along an inserted rod.
Figure 24:
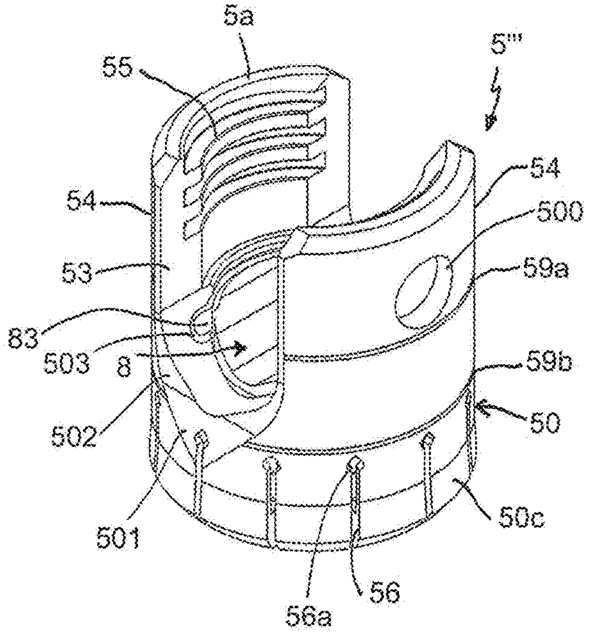
FIG. 24 shows a perspective view from a top of the receiving part of the polyaxial bone anchoring device of FIGS. 21 to 23.
Figure 25:
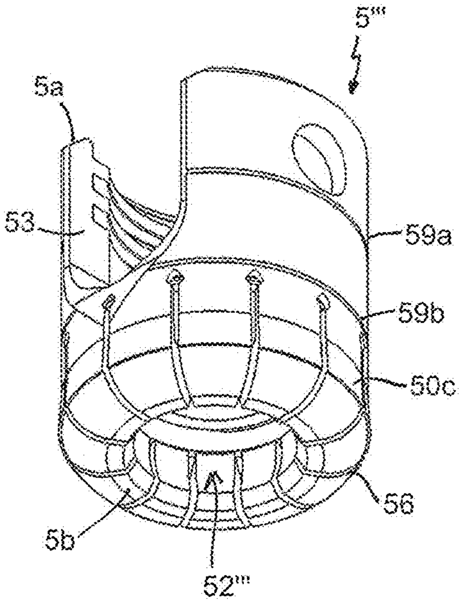
FIG. 25 shows a perspective view from a bottom of the receiving part of FIG. 24.
Figure 26:
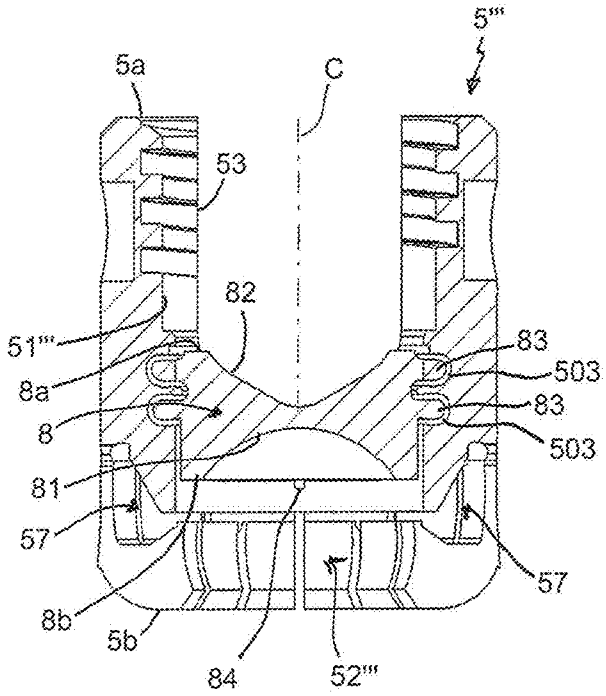
FIG. 26 shows a cross-sectional view of the receiving part of FIGS. 24 and 25, the cross-section being taken perpendicular to the rod channel, similar to the cross-section in FIG. 22.
Figure 27:
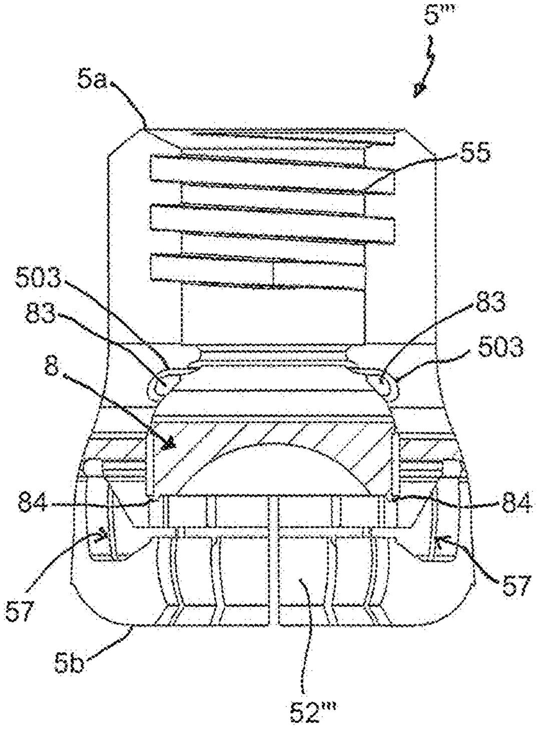
FIG. 27 shows a cross-sectional view of the receiving part of FIGS. 24 to 26, the cross-section being taken along the rod channel, similar to the cross-section in FIG. 23.
Figure 28:
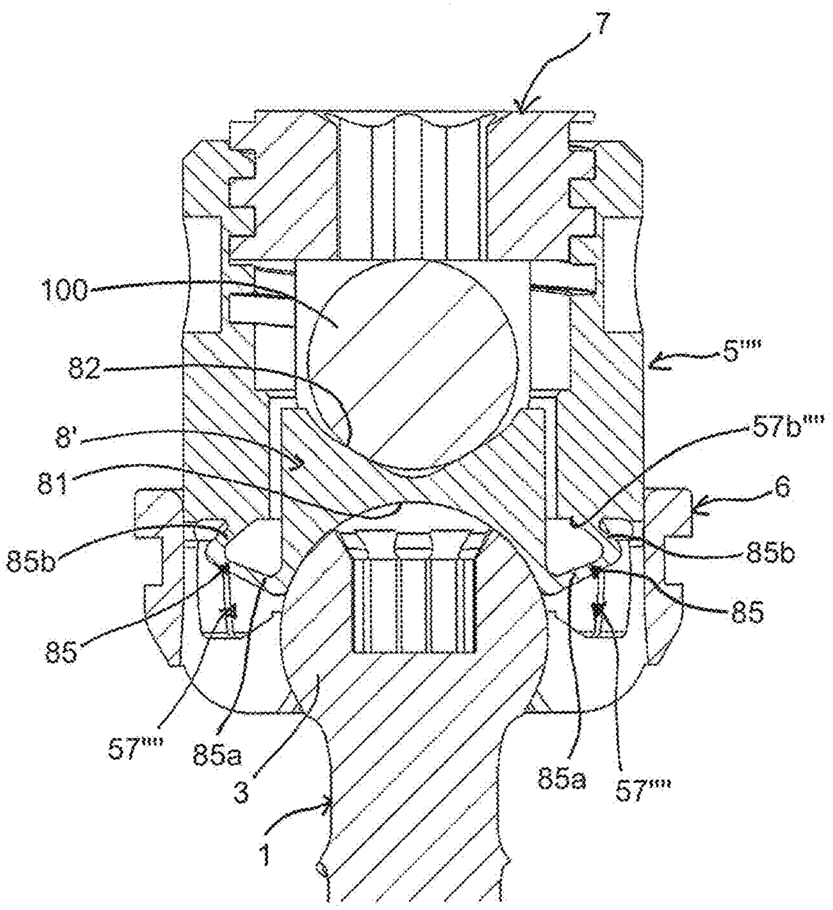
FIG. 28 shows a cross sectional view of a still further embodiment of a polyaxial bone anchoring device, the cross-section taken in a plane extending through legs of the receiving part and perpendicular to an inserted rod.
Figure 29:
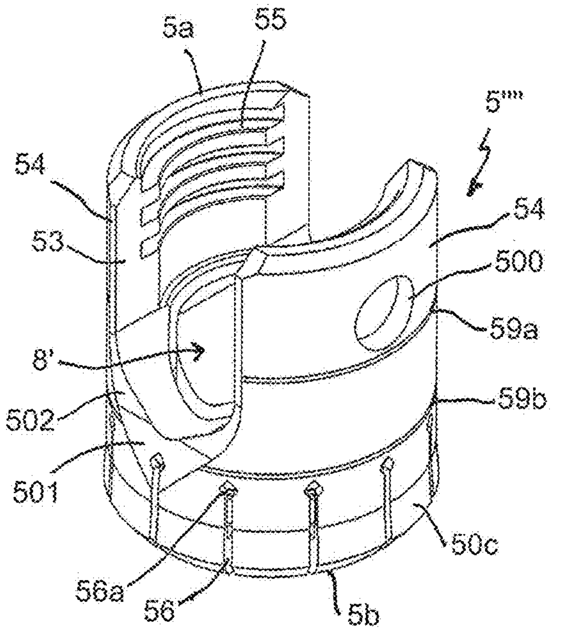
FIG. 29 shows a perspective view from a top of the receiving part of the polyaxial bone anchoring device of FIG. 28.
Figure 30:
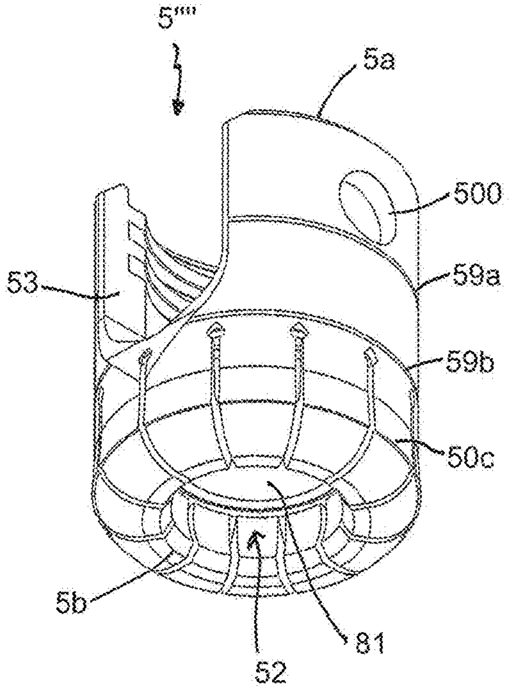
FIG. 30 shows a perspective view from a bottom of the receiving part of FIG. 29.
Figure 31:
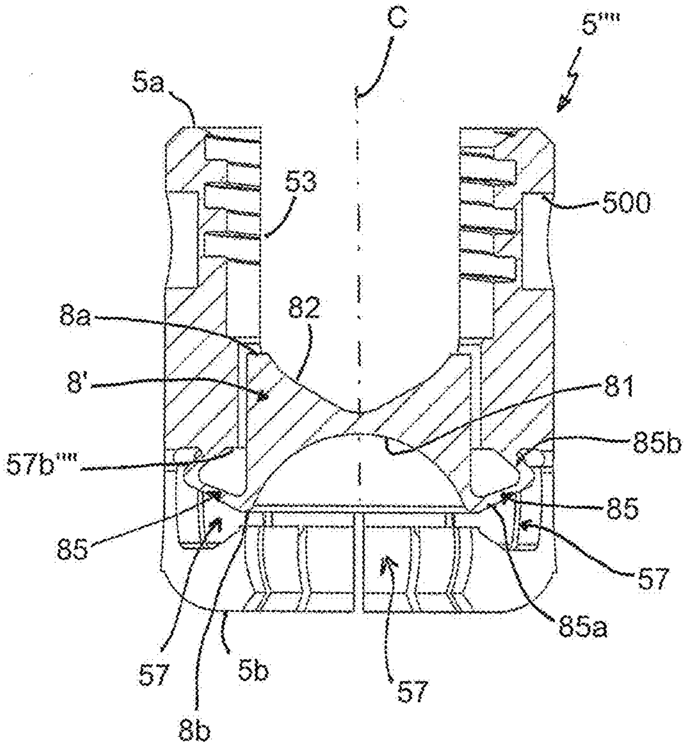
FIG. 31 shows a cross-sectional view of the receiving part of FIGS. 29 and 30, the cross-section being taken perpendicular to the rod channel, similar to the cross-section of FIG. 28.
Figure 32:
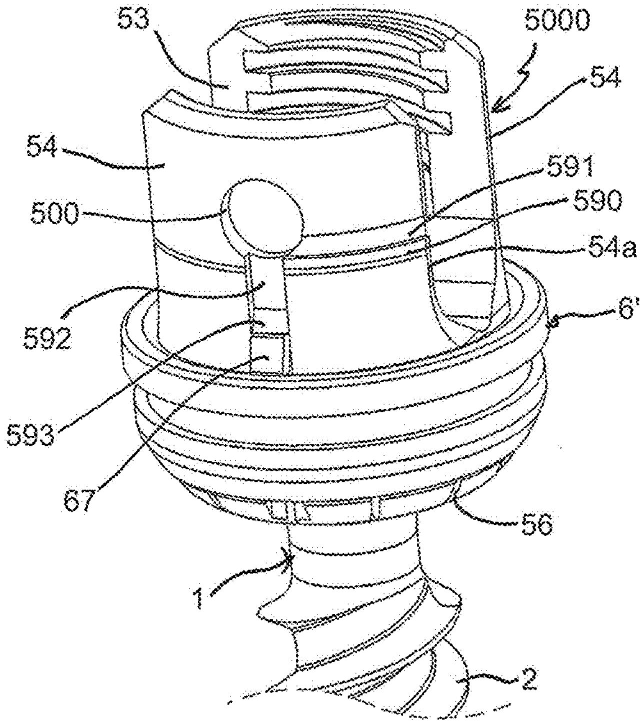
FIG. 32 shows a perspective view of a yet still further embodiment of a polyaxial bone anchoring device in an assembled state.

The pressure member 8 is monolithically connected to the receiving part 5''', with one or more connection portions 84 that may be arranged at approximately 90°" from centers of the legs 54 in a circumferential direction, on both sides of the rod channel, as can be seen in particular in FIGS. 23 and 27. The connection portion 84 is thin so that it can be easily broken when a force is exerted onto the pressure member 8. Thus, the connection portion 84 forms a predefined breaking region that is configured to break under load, so that the pressure member 8 can be separated from the receiving part 5'''. The receiving part 5''' and the pressure member 8 are manufactured preferably as a monolithic part, for example, by using an additive manufacturing method as described above.

It shall be noted that the pressure member 8 lacks a central hole that provides access to the head 3. Hence, the polyaxial bone anchoring device in the embodiment of FIGS. 21 to 27 is particularly suitable for in-situ placement of the bone anchoring element 1 into bone, and then mounting the receiving part with assembled locking ring thereafter. In a still further modified embodiment, the pressure member 8 may have a central hole providing access to the head 3 with a tool.

Figure 22:
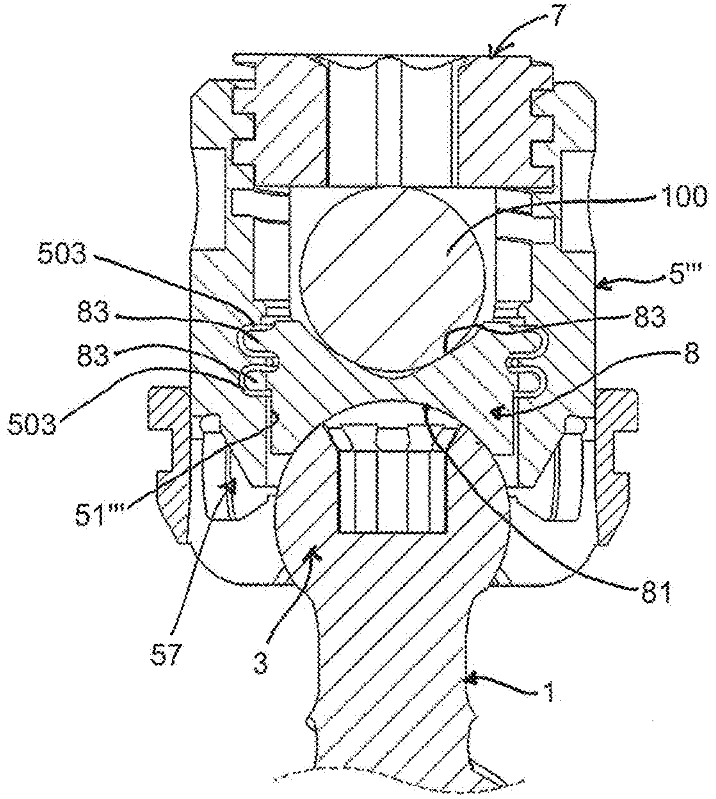
FIG. 22 shows a cross-sectional view of the polyaxial bone anchoring device of FIG. 21, the cross-section being taken in a plane extending through centers of legs of the receiving part and perpendicular to an inserted rod.

In use, as shown in FIGS. 22 and 23, the head 3 is first inserted into the receiving part 5''' and clamped by means of the locking ring 6, which is moved into the locking position where the tapered surfaces 50*c* and 63 of the receiving part and the locking ring, respectively, are engaged. Then, the rod 100 is inserted until it rests on the rod support surface of the recess 82 of the pressure member 8. Finally, the fixation member 7 is inserted between the legs and tightened. The pressure exerted by the fixation member 7 onto the rod 100 is transferred onto the pressure member 8. Thereby, the connection portion 84 breaks and the pressure member 8 can move to some extent in the axial direction, so that the pressure is transferred via the pressure member 8 to the head 3 to finally lock the head in the head receiving portion 50. Due to the axial play, the pressure member can move slightly downward. Due to the radial and the axial play, the pressure member 8 can also be tilted slightly or wobble with respect to the head 3. This permits adjusting of pressures more precisely.

Referring to FIGS. 28 to 31, a still further embodiment of the polyaxial bone anchoring device is described. The receiving part 5'''' is similar to the receiving part 5''' of the previous embodiment, except with respect to the shape and connection to the pressure member 8' and the shape of the cavity. The pressure member 8' is permanently connected to the receiving part 5''''. In order to render the pressure member 8' movable, the pressure member 8' includes a spring portion 85 that connects the pressure member 8' and the receiving part 5'''' monolithically in a resilient manner. The spring portion 85 is formed by two portions forming an angle. In greater detail, the spring portion includes a first portion 85*a* that extends from the outer edge of the second end 8*b* of the pressure member in an inclined manner upwards towards the first end 5*a* of the receiving part, and a second portion 85*b* that extends from the first portion 85*a* in an oppositely inclined manner to a downwardly facing upper wall portion 57*b*'''' of the cavity 57''''. The cavity 57'''' has a large opening that opens into the passage to accommodate the spring portion 85. Due to its shape, the spring portion 85 provides resiliency to the pressure member 8' in the axial direction and also to some extent in the radial direction. Preferably, the pressure member 8' and the receiving part 5'''' are manufactured monolithically, for example, by using an additive manufacturing method.

In use, when the head has been inserted into the head receiving portion and the rod has been inserted into the rod channel and rests on the rod support surface of the recess 82, tightening of the fixation member 7 transfers the pressure via the rod onto the pressure member 8' and finally onto the head 3, so that the head is locked in the accommodation space.

Loosening the fixation member also loosens the clamping of the head. For example, when the locking ring is in the pre-locking position, several correction steps can be carried out in this manner, before final locking.

Referring to FIGS. 32 to 37, a still further embodiment of the polyaxial bone anchoring device is shown that is modified with respect to the cooperation of the receiving part with the locking ring. Parts and portions that are identical or similar to those of the embodiment according to FIGS. 1 to 12*f* are designated with the same reference numerals, and the descriptions thereof will not be repeated.

The locking ring 6' has, at a particular position in the circumferential direction, an extension portion 67 that extends from the first end 6*a* in a direction above the first end. The extension portion 67 may be inclined towards the central axis and may be resilient to some extent. In the illustrated embodiment, the extension member 67 has a substantially rectangular cross-section.

The receiving part 5000 is different from the receiving part 5 of FIGS. 1 to 12*f* in the design of the holding structures at the outer surface of the receiving part. A first holding structure includes a rib 590 that is located above the bottom 53*a* of the substantially U-shaped recess 53 and at a distance from the first end 5*a*. The rib 590 extends only over about half a leg 54 from one edge 54*a* of one leg 54 in a circumferential direction up to the through hole 500. Adjacent to the rib 590, at the side towards the first end 5*a*, is a groove 591 that runs concentrically with the rib 590. The groove 591 provides space for the free end of the extension portion 67 of the locking ring. Further, a guiding groove 592 is formed that extends from the through hole 500 in the axial direction downward to the second end 5*b* of the receiving part. At a distance from the through hole 500, a downwardly inclined ramp or obstacle 593 that widens downwardly is provided in the groove 592. The ramp 593 permits the extension portion 67 to snap over the ramp when moving downward, but prevents the extension portion 67 from moving upward again after passing downwardly past it. The ramp 593 is located at an axial position such that the locking ring is in the pre-locking position when the extension portion 67 has passed downwardly past the ramp 593.

A mounting groove 595 is formed at the receiving part 5000 at a side of the rod channel. In greater detail, the mounting groove 595 extends from the second end 5*b* up to a small distance from the bottom 53*a* of the substantially U-shaped recess 53. The mounting groove 595 permits the extension portion 67 to extend therein when the locking ring 6' is mounted to the receiving part from the second end 5*b*.

Figure 33D:
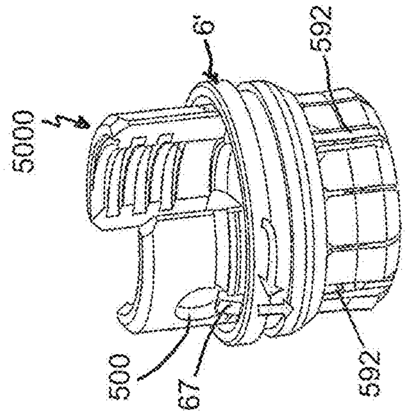
FIGS. 33*a* to 33*d* show perspective views of a receiving part and a locking ring of the polyaxial bone anchoring device of FIG. 32, and steps of mounting and operating the locking ring of the polyaxial bone anchoring device of FIG. 32.
Figure 33C:
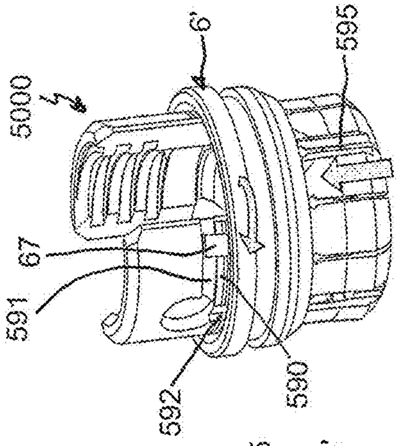
Figure 33B:
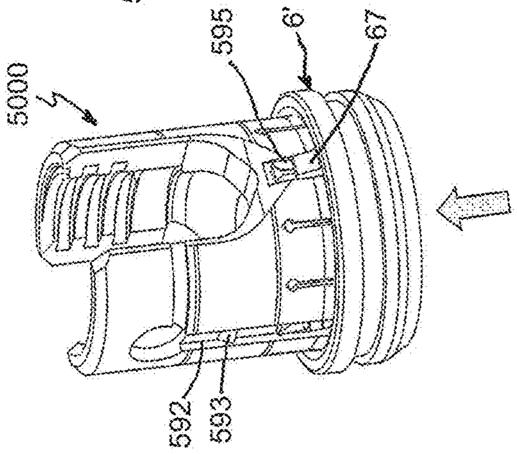
Figure 33A:
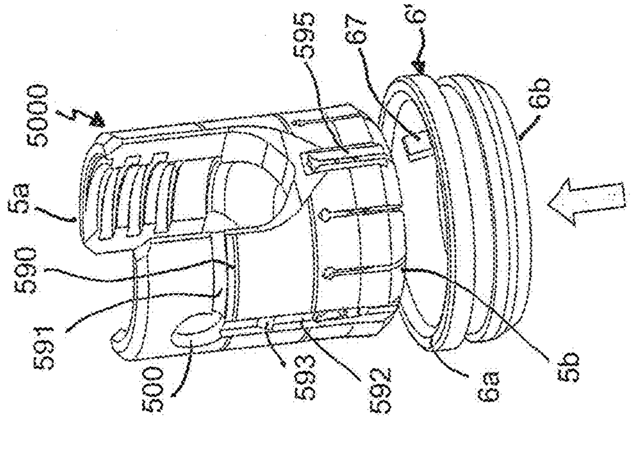
Figure 34:
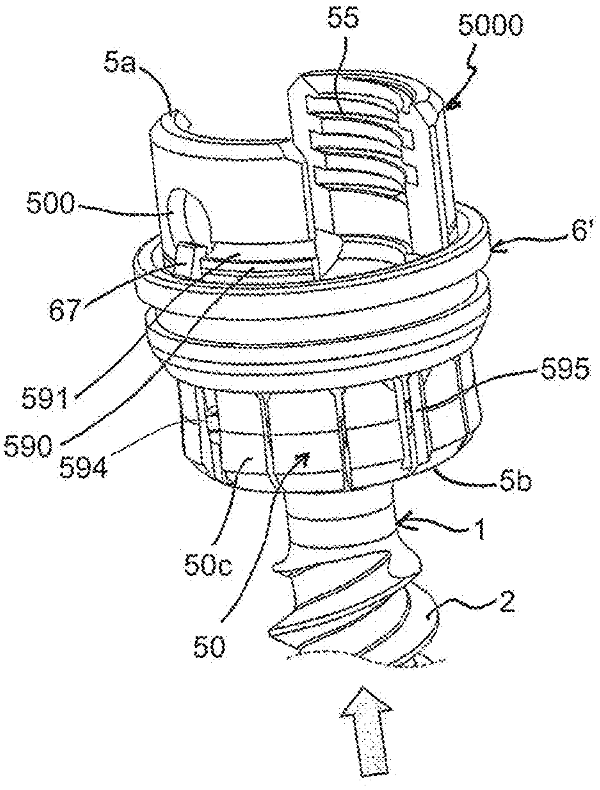
FIGS. 34 and 35 show perspective views of steps of locking a head in the receiving part of the polyaxial bone anchoring device of FIG. 32.
Figure 36:
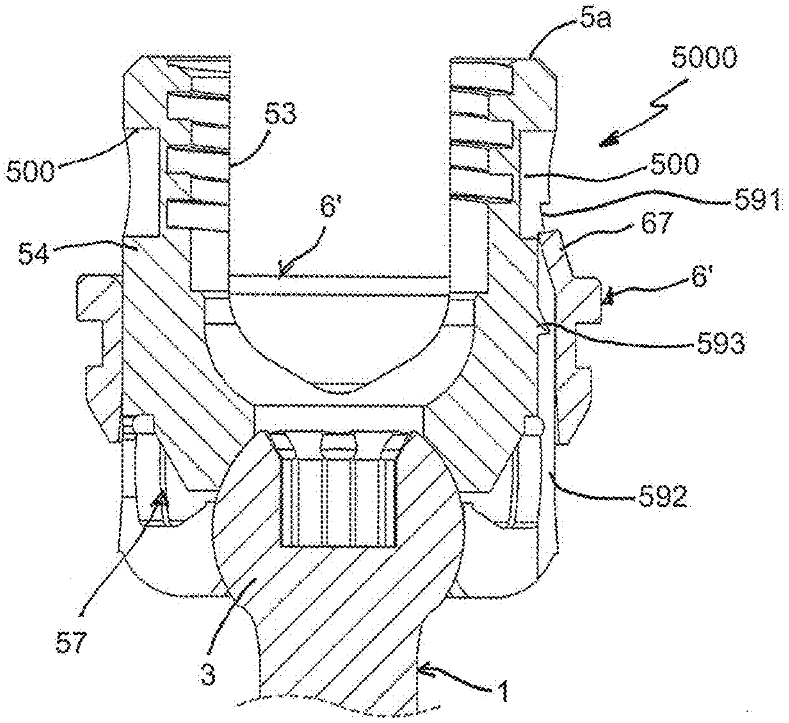
FIGS. 36 and 37 show cross-sectional views of steps of locking the head in the receiving part of the polyaxial bone anchoring device of FIG. 32, the cross-sections corresponding to FIGS. 34 and 35, respectively.

As shown in FIGS. 33*a* to 33*d*, the locking ring 6' can be mounted to the receiving part 5000 from the second end 5*b* of the receiving part in an orientation in which the extension portion 67 is aligned with the mounting groove 595. The extension portion 67 engages the mounting groove 595 and the locking ring 6' is moved upwards as depicted in FIG. 33*b*. When the extension portion 67 has reached the circumferentially extending groove 591, the locking ring 6' is rotated until the extension portion 67 snaps into the through hole 500. In this position, the extension portion 67 engages the bottom of the edge of the through hole 500, as also shown in FIGS. 34 and 36, and is temporarily held there in the insertion position where the head can be inserted.

Figure 35:
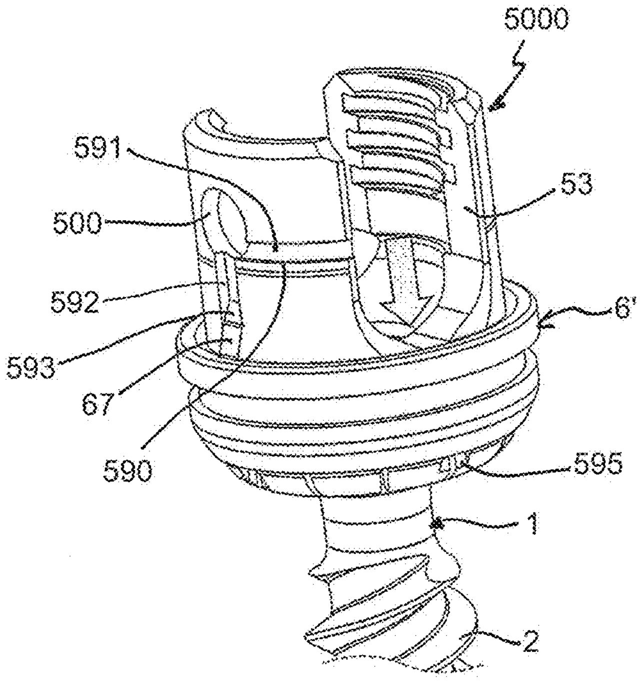
Figure 37:
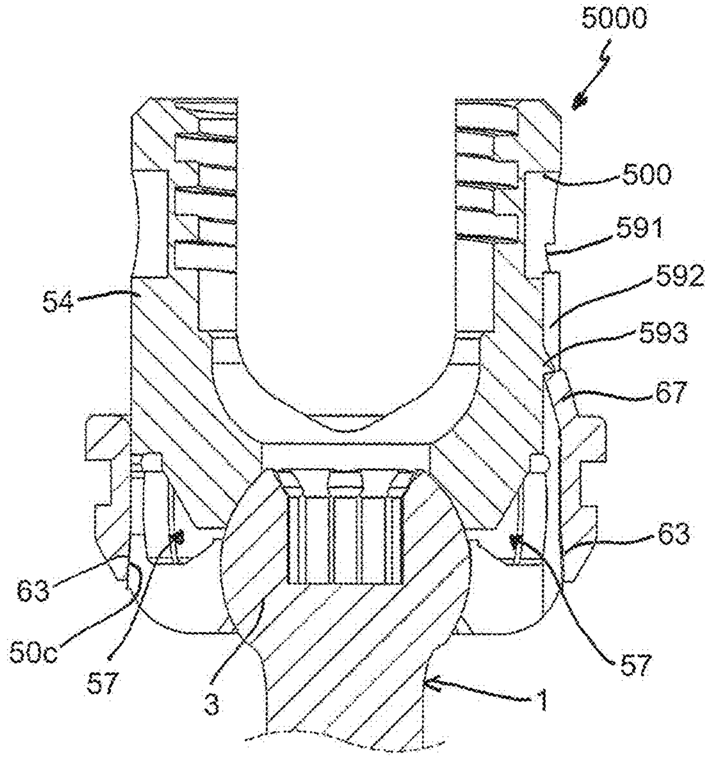

Once the head is inserted into the accommodation space 52 of the head receiving portion, the locking ring 6' can be moved downward until the extension portion 67 snaps over the ramp 593 into the pre-locking position, as shown in FIGS. 35 and 37. In the pre-locking position the head cannot be removed from the receiving part. Thereafter, the locking ring can be moved further downward until the head 3 is locked.

Additional modifications of the embodiments are also conceivable. The parts are not limited to their detailed shape as depicted in the embodiments. The features of the various embodiments can be combined with each other to produce a number of further embodiments. In particular, the detailed shapes of the passage and the cavity in the receiving part may vary. Also, the receiving part and/or the head may be designed such that the head can only pivot in preferred directions and/or can pivot in one direction to a greater maximum angle than in another direction. For the bone anchoring element, all kinds of bone anchoring elements can be used, such as screws, nails, etc.

While the present invention has been described in connection with certain exemplary embodiments, it is to be understood that the invention is not limited to the disclosed embodiments, but is instead intended to cover various modifications and equivalent arrangements included within the spirit and scope of the appended claims, and equivalents thereof.

What is claimed is:

1. A receiving part for a polyaxial bone anchoring device, the receiving part having a first end, a second end, and a central axis that extends through the first and second ends, and comprising:

a rod receiving portion at the first end defining a recess for receiving a rod, the recess extending from the first end towards the second end and forming two legs; and a head receiving portion at the second end comprising a wall, wherein the wall has an outer surface that faces radially away from the central axis, and defines an accommodation space for accommodating a head of an anchoring element, at least one cavity located radially between the accommodation space and the outer surface for reducing a radial thickness of at least part of the wall, and an opening that extends between and that connects the cavity with the accommodation space;

wherein part of the wall extends between the cavity and the outer surface, and wherein a maximum axial height of the opening measured in a first direction parallel to the central axis is less than an axial height of the cavity measured in the first direction.

2. The receiving part of claim 1, wherein the cavity extends in the circumferential direction at least partially around the accommodation space.

3. The receiving part of claim 2, wherein the cavity extends entirely around the accommodation space in the circumferential direction.

4. The receiving part of claim 1, wherein the cavity extends from an axial position above a region corresponding to a largest outer diameter of the inserted head to an axial position below the region corresponding to the largest outer diameter of the inserted head.

5. The receiving part of claim 1, wherein the opening comprises a slit.

6. The receiving part of claim 1, wherein the second end of the receiving part defines an opening for inserting the head into the accommodation space, and wherein at least a portion of the wall around the accommodation space is expandable in the radial direction.

7. A polyaxial bone anchoring device comprising the receiving part of claim 1 and a locking member positionable at least partially around the receiving part.

8. The polyaxial bone anchoring device of claim 7, wherein the locking member is adjustable to lock an inserted head in the accommodation space.

9. A receiving part for a polyaxial bone anchoring device, the receiving part having a first end, a second end below the first end, and a central axis that extends through the first and second ends, and comprising:

a rod receiving portion at the first end defining a recess for receiving a rod, the recess extending from the first end towards the second end and forming two legs; and a head receiving portion at the second end that defines an accommodation space for accommodating a head of an anchoring element, wherein the accommodation space has a downwardly facing surface configured to face an upper portion of the head when the head is held in the accommodation space, and a radially expandable portion defining a seat for holding the head in the accommodation space, wherein a portion of the seat that is oriented in a first radial direction relative to the central axis is radially expandable independently relative to a portion of the downwardly facing surface that is oriented in the first radial direction;

wherein at least part of the radially expandable portion is configured to extend upwardly to an axial position that is closer to the first end of the receiving part than at least part of the downwardly facing surface is to the first end of the receiving part.

10. The receiving part of claim 9, wherein at least one cavity separates the downwardly facing surface and the radially expandable portion from one another.

11. The receiving part of claim 10, wherein the cavity extends entirely around the accommodation space in the circumferential direction.

12. The receiving part of claim 9, wherein the second end of the receiving part defines an opening for inserting the head into the accommodation space.

13. The receiving part of claim 9, wherein the head receiving portion further defines a plurality of axially extending slits open to the second end of the receiving part that form flexible wall sections of the head receiving portion, with portions closer to the second end that are thicker radially than portions farther from the second end.

14. The receiving part of claim 9, wherein the downwardly facing surface is formed on a pressure member that is monolithically formed with the receiving part and that is movable axially relative to the seat to clamp the head therebetween.

15. A polyaxial bone anchoring device comprising:

a receiving part having a first end, a second end, and a central axis that extends through the first and second ends, the receiving part comprising a rod receiving portion at the first end defining a recess for receiving a rod, and a head receiving portion at the second end that defines an accommodation space for accommodating a head of an anchoring element; and a locking member positionable at least partially around the receiving part;

wherein when the locking member is assembled to the receiving part, the locking member is rotatable relative to the receiving part from a first rotational orientation while at a first axial position relative to the receiving part where the locking member is axially separable from the receiving part to a second rotational orientation while remaining substantially at the first axial position where the locking member is restricted from being separated axially from the receiving part, and wherein when the locking member is at the second rotational orientation, the locking member is movable axially from the first axial position to a second axial position relative to the receiving part where the locking member is restricted from being rotated to the first rotational orientation.

16. The polyaxial bone anchoring device of claim 15, wherein the second end of the receiving part defines an opening for inserting the head into the accommodation space.

17. The polyaxial bone anchoring device of claim 15, wherein the head receiving portion further defines a plurality of axially extending slits open to the second end of the receiving part that form flexible wall sections of the head receiving portion.

18. The polyaxial bone anchoring device of claim 15, wherein the locking member is adjustable to lock an inserted head in the accommodation space.

19. The polyaxial bone anchoring device of claim 15, wherein the locking member forms a closed ring positionable around the head receiving portion.

20. The polyaxial bone anchoring device of claim 15, wherein when the locking member is at the second rotational orientation and the second axial position, the receiving part and/or the locking member comprises a holding structure for restricting the locking member from moving axially back to the first axial position.

* * * * *